US011931259B2

(12) United States Patent
Le et al.

(10) Patent No.: US 11,931,259 B2
(45) Date of Patent: Mar. 19, 2024

(54) EXPANDABLE SHEATH AND METHODS OF USING THE SAME

(71) Applicant: Edwards Lifesciences Corporation, Irvine, CA (US)

(72) Inventors: Thanh Huy Le, Oceanside, CA (US); Tung T. Le, Costa Mesa, CA (US); Sovanpheap Mak, Santa Ana, CA (US); Alpana Kiran Gowdar, Irvine, CA (US); Richard D. White, Costa Mesa, CA (US); Sonny Tran, Westminster, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 566 days.

(21) Appl. No.: 16/865,656

(22) Filed: May 4, 2020

(65) Prior Publication Data

US 2020/0261227 A1    Aug. 20, 2020

Related U.S. Application Data

(63) Continuation of application No. 16/010,744, filed on Jun. 18, 2018, now Pat. No. 10,639,152.
(Continued)

(51) Int. Cl.
*A61F 2/24* (2006.01)
*A61M 25/00* (2006.01)
(Continued)

(52) U.S. Cl.
CPC ....... *A61F 2/2436* (2013.01); *A61M 25/0009* (2013.01); *B29C 65/00* (2013.01);
(Continued)

(58) Field of Classification Search
CPC .............. B29D 23/00; B29C 65/00; A61M 2025/0024; A61M 2025/0098;
(Continued)

(56) References Cited

U.S. PATENT DOCUMENTS

| 4,035,849 A | 7/1977 | Angell et al. |
| 4,592,340 A | 6/1986 | Boyles |

(Continued)

FOREIGN PATENT DOCUMENTS

| CN | 105188620 A | 12/2015 |
| CN | 106473839 A | 3/2017 |

(Continued)

*Primary Examiner* — Yan Lan
(74) *Attorney, Agent, or Firm* — Jessica A. Keesee; MEUNIER CARLIN & CURFMAN LLC

(57) ABSTRACT

Disclosed herein are expandable introducer sheaths and methods of making and using the same. The sheaths minimize trauma to a patient's vasculature by allowing for temporary expansion of a portion of the sheath to accommodate passage of a delivery system for an implant, then return to a non-expanded state after the passage of the device. The sheath includes a foldable inner member having a detached flap structure at its distal tip that facilitates expansion of the sheath lumen to increased diameters, and an elastomeric distal end that reduces push and retrieval forces therethrough. The sheath can include a hemostasis seal on its proximal end to prevent the leakage of blood out of the sheath and prevent ballooning of outer layer of the sheath.

16 Claims, 12 Drawing Sheets

Related U.S. Application Data

(60) Provisional application No. 62/522,986, filed on Jun. 21, 2017.

(51) Int. Cl.
  *B29C 65/00* (2006.01)
  *B29D 23/00* (2006.01)
  *A61M 39/06* (2006.01)

(52) U.S. Cl.
  CPC ...... *B29D 23/00* (2013.01); *A61F 2250/0003* (2013.01); *A61F 2250/0098* (2013.01); *A61M 39/06* (2013.01); *A61M 2039/0626* (2013.01)

(58) Field of Classification Search
  CPC ...... A61M 2039/0626; A61M 25/0009; A61M 25/0662; A61M 39/06; A61F 2/2436; A61F 2250/0003; A61F 2250/0098
  See application file for complete search history.

(56) References Cited

U.S. PATENT DOCUMENTS

| | | |
|---|---|---|
| 4,994,077 A | 2/1991 | Dobben |
| 5,059,177 A | 10/1991 | Towne et al. |
| 5,201,756 A | 4/1993 | Horzewski et al. |
| 5,318,588 A | 6/1994 | Horzewski et al. |
| 5,411,552 A | 5/1995 | Andersen et al. |
| 5,554,185 A | 9/1996 | Block et al. |
| 5,591,195 A | 1/1997 | Taheri et al. |
| 5,599,305 A | 2/1997 | Hermann et al. |
| 5,639,274 A | 6/1997 | Fischell et al. |
| 5,728,068 A | 3/1998 | Leone et al. |
| 5,840,081 A | 11/1998 | Andersen et al. |
| 5,968,068 A | 10/1999 | Dehdashtian et al. |
| 6,168,614 B1 | 1/2001 | Andersen et al. |
| 6,217,585 B1 | 4/2001 | Houser et al. |
| 6,379,372 B1 | 4/2002 | Dehdashtian et al. |
| 6,454,799 B1 | 9/2002 | Schreck |
| 6,458,153 B1 | 10/2002 | Bailey et al. |
| 6,461,382 B1 | 10/2002 | Cao |
| 6,527,979 B2 | 3/2003 | Constantz et al. |
| 6,582,462 B1 | 6/2003 | Andersen et al. |
| 6,652,578 B2 | 11/2003 | Bailey et al. |
| 6,730,118 B2 | 5/2004 | Spenser et al. |
| 6,733,525 B2 | 5/2004 | Yang et al. |
| 6,767,362 B2 | 7/2004 | Schreck |
| 6,830,584 B1 | 12/2004 | Seguin |
| 6,893,460 B2 | 5/2005 | Spenser et al. |
| 6,908,481 B2 | 6/2005 | Cribier |
| 7,018,406 B2 | 3/2006 | Seguin et al. |
| 7,018,408 B2 | 3/2006 | Bailey et al. |
| 7,276,084 B2 | 10/2007 | Yang et al. |
| 7,318,278 B2 | 1/2008 | Zhang et al. |
| 7,374,571 B2 | 5/2008 | Pease et al. |
| 7,393,360 B2 | 7/2008 | Spenser et al. |
| 7,510,575 B2 | 3/2009 | Spenser et al. |
| 7,585,321 B2 | 9/2009 | Cribier |
| 7,618,446 B2 | 11/2009 | Andersen et al. |
| 7,785,366 B2 | 8/2010 | Maurer et al. |
| 7,959,661 B2 | 6/2011 | Hijlkema et al. |
| 8,029,556 B2 | 10/2011 | Rowe |
| 8,167,932 B2 | 5/2012 | Bourang et al. |
| 8,449,606 B2 | 5/2013 | Eliasen et al. |
| 2002/0032481 A1 | 3/2002 | Gabbay |
| 2003/0050694 A1 | 3/2003 | Yang et al. |
| 2004/0133263 A1 | 7/2004 | Dusbabek et al. |
| 2004/0186563 A1 | 9/2004 | Lobbi |
| 2004/0186565 A1 | 9/2004 | Schreck |
| 2004/0260389 A1 | 12/2004 | Case et al. |
| 2005/0080474 A1 | 4/2005 | Andreas et al. |
| 2005/0096736 A1 | 5/2005 | Osse et al. |
| 2005/0203614 A1 | 9/2005 | Forster et al. |
| 2005/0203617 A1 | 9/2005 | Forster et al. |
| 2006/0025857 A1 | 2/2006 | Bergheim et al. |
| 2007/0005131 A1 | 1/2007 | Taylor |
| 2007/0203575 A1 | 8/2007 | Forster et al. |
| 2007/0265700 A1 | 11/2007 | Eliasen et al. |
| 2008/0125853 A1 | 5/2008 | Bailey et al. |
| 2008/0294230 A1 | 11/2008 | Parker |
| 2009/0157175 A1 | 6/2009 | Benichou |
| 2009/0276040 A1 | 11/2009 | Rowe et al. |
| 2009/0281619 A1 | 11/2009 | Le et al. |
| 2009/0319037 A1 | 12/2009 | Rowe et al. |
| 2010/0049313 A1 | 2/2010 | Alon et al. |
| 2010/0198347 A1 | 8/2010 | Zakay et al. |
| 2010/0324490 A1 | 12/2010 | Pini et al. |
| 2011/0015729 A1 | 1/2011 | Jimenez et al. |
| 2012/0083877 A1 | 4/2012 | Nguyen et al. |
| 2012/0123529 A1 | 5/2012 | Levi et al. |
| 2013/0317598 A1 | 11/2013 | Rowe et al. |
| 2016/0074067 A1 | 3/2016 | Furnish et al. |
| 2016/0296730 A1 | 10/2016 | Zhou et al. |

FOREIGN PATENT DOCUMENTS

| | | |
|---|---|---|
| DE | 19532846 A1 | 3/1997 |
| DE | 19907646 A1 | 8/2000 |
| EP | 0592410 B1 | 10/1995 |
| EP | 0850607 A1 | 7/1998 |
| FR | 2815844 A1 | 5/2002 |
| WO | 9117720 A1 | 11/1991 |
| WO | 9829057 A1 | 7/1998 |
| WO | 0149213 A2 | 7/2001 |
| WO | 0154625 A1 | 8/2001 |
| WO | 0176510 A2 | 10/2001 |
| WO | 0222054 A1 | 3/2002 |
| WO | 0236048 A1 | 5/2002 |
| WO | 0247575 A2 | 6/2002 |
| WO | 03047468 A1 | 6/2003 |
| WO | 2005084595 A1 | 9/2005 |
| WO | 2006032051 A2 | 3/2006 |
| WO | 2006111391 A1 | 10/2006 |
| WO | 2006138173 A3 | 3/2007 |
| WO | 2005102015 A3 | 4/2007 |
| WO | 2007047488 A2 | 4/2007 |
| WO | 2007067942 A1 | 6/2007 |
| WO | 2010121076 A2 | 10/2010 |

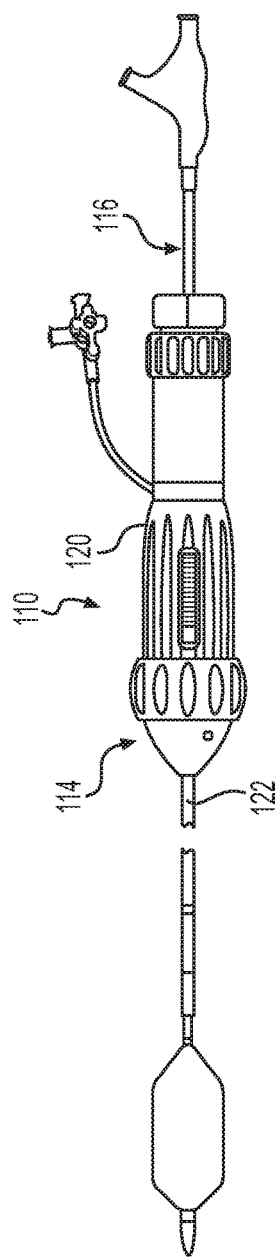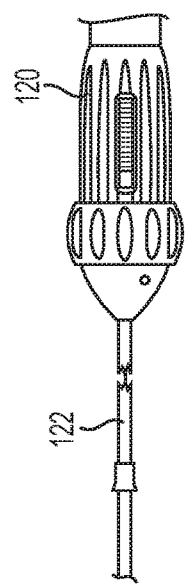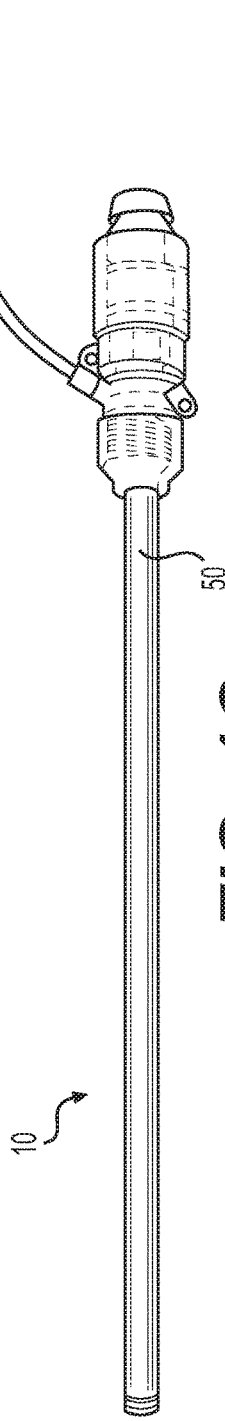
FIG. 1A
FIG. 1B
FIG. 1C

EXPANDABLE SHEATH AND METHODS OF USING THE SAME

CROSS REFERENCE TO RELATED APPLICATIONS

This application is a continuation of U.S. application Ser. No. 16/010,744, filed Jun. 18, 2018, which claims priority to U.S. Provisional Application No. 62/522,986, filed Jun. 21, 2017, which is incorporated by reference in its entirety for all purposes.

FIELD

The present application concerns embodiments of a sheath for use with catheter-based technologies to introduce a prosthetic device, such as a heart valve or other implant, into the patient's vasculature.

BACKGROUND

Endovascular delivery catheter assemblies are used to implant prosthetic devices, such as a prosthetic heart valve, at locations inside the body that are not readily accessible by surgery or where access without invasive surgery is desirable. For example, aortic, mitral, tricuspid, and/or pulmonary prosthetic valves can be delivered to a treatment site using minimally invasive surgical techniques, including transcatheter delivery methods.

An introducer sheath can be used to safely introduce a delivery apparatus into a patient's vasculature (e.g., the femoral artery). An introducer sheath generally has an elongated sleeve that is inserted into the vasculature and a housing that contains one or more sealing valves that allow a delivery apparatus to be placed in fluid communication with the vasculature with minimal blood loss. A conventional introducer sheath typically requires a tubular loader to be inserted through the seals in the housing to provide an unobstructed path through the housing for the prosthetic implant, such as a heart valve mounted on a balloon catheter. A conventional loader extends from the proximal end of the introducer sheath, and therefore decreases the available working length of the delivery apparatus that can be inserted through the sheath and into the body.

Conventional methods of accessing a vessel, such as a femoral artery, prior to introducing the delivery system include dilating the vessel using multiple dilators or sheaths that progressively increase in diameter. This repeated insertion and vessel dilation can increase the amount of time the procedure takes, as well as the risk of damage to the vessel.

Radially expanding intravascular sheaths reduce the overall profile of the sheath to reduce risk of damage to the vessel. Such sheaths tend to have complex mechanisms, such as ratcheting mechanisms that maintain the shaft or sheath in an expanded configuration once a device with a larger diameter than the sheath's original diameter is introduced.

However, delivery and/or removal of prosthetic devices and other material to or from a patient still poses a risk to the patient. Furthermore, accessing the vessel remains a challenge due to the relatively large profile of the delivery system that can cause longitudinal and radial tearing of the vessel during insertion. The delivery system can additionally dislodge calcified plaque within the vessels, posing an additional risk of clots caused by the dislodged plaque. The addition of radially expanding properties can also hinder a practitioner's ability to push the sheath without it bending or kinking. Thus, there remains a need for further improvements in introducer sheaths for endovascular systems used for implanting heart valves and other prosthetic devices.

SUMMARY

Disclosed herein are expandable introducer sheaths and methods of making and using the same. The expandable introducer sheaths disclosed herein are used to deliver a prosthetic device through a patient's vasculature to a procedure site within the body. The sheath is constructed to be highly expandable and collapsible in the circumferential direction, while also minimizing the wall thickness of the sheath to minimize the profile of the delivery system. In addition, the sheath disclosed herein includes a distal tip assembly that benefits from use of a flap instead of a folding configuration to reduce the layers of the tip while at the same time allowing for enhanced expansion diameters of 30% or more for passing implants. The flap assembly in the distal tip also allows enhanced ease of expansion for balloon and implant retrieval. Further disclosed herein is a proximally located seal for mediating leakage of blood between the outer elastomeric layer and inner folding layer. The seal's proximal location reduces the layers, bumps and asymmetries at the tip and the seal is preferably marked for positioning at or near the entry into the patient's vasculature to mediate ballooning or leaks. Also, the seal assembly can include an outer jacket to enhance visibility of the seal location and guard against ballooning adjacent the seal.

Some embodiments include an expandable sheath having an elongated inner member and an elastomeric outer member. The elongated inner member defines a central lumen and first and second circumferential portions. The first circumferential portion includes first and second longitudinal edges. The second circumferential portion extends between the first and second longitudinal edges. The elongated inner member is configured to crease at the first and second longitudinal edges into a folded configuration. The second circumferential portion, in the folded configuration, is positioned at least partially between the overlapping edges. The outer elastomeric member extends around the elongated inner member and is configured to bias the elongated inner member into the folded configuration. The elongated inner member also includes a distal tip. The distal tip includes a flap extending from the first longitudinal edge at least to the second longitudinal edge in an open (or at least partially unfolded) configuration of the elongated inner member.

In other embodiments, the flap is configured to slide circumferentially over an outer surface of the first circumferential portion when the elongated member is biased into the folded configuration by the elastic member. The second circumferential portion can have a distal edge extending longitudinally at least to a proximal edge of the flap. The proximal edge of the flap can extend over the distal edge of the second circumferential portion onto an outer surface of the second circumferential portion.

The flap in another embodiment can include a longitudinal section of the second circumferential portion cut along the second longitudinal edge. The longitudinal section can also be cut circumferentially from the distal end of the second circumferential portion.

In other embodiments, the expandable sheath can also include an overlap extension. The overlap extension, for example, can extend circumferentially from the longitudinal section. Also the overlap extension can extend proximally from the longitudinal section.

In other embodiments, the distal tip can further include an elastomeric end extending from a distal end of the elongated inner member. The elastomeric end can include a distally tapering shape. Also, the distal tip can include a marker embedded therein, such as in the inner member.

Also disclosed is a method of making a distal tip of an expandable sheath. The method includes forming a folded configuration in an elongated inner member by forming a crease along a first longitudinal edge and a second longitudinal edge of the elongated inner member. The first circumferential portion is positioned at least partially between the longitudinal edges in the folded configuration. Also, the method includes forming a flap on a distal tip of an inner member so that the flap extends from a first longitudinal edge of the inner member at least to a second longitudinal edge of the inner member. Further, the method can include covering the elongated inner member with an elastomeric outer member.

The method can include other embodiments, such as extending the flap circumferentially over an outer surface of the first circumferential portion when forming the flap. Forming the flap can also include forming a proximal edge on the flap that extends over a distal edge and onto an outer surface of the second circumferential portion. The flap can also be formed at least partially by cutting a longitudinal section from the second circumferential portion. And, the flap can be formed, at least partially, by attaching an overlap extension to the longitudinal section.

The method can also include attaching an elastomeric end to a distal end of the elongated inner member. And, the method can include forming a tapered shape into the elastomeric end.

In other embodiments, a method of delivering a prosthetic device, such as heart valve, is disclosed. The method can include positioning an expandable sheath within the vascular system of the patient. And, the method includes introducing a prosthetic device through the lumen of the expandable sheath such that the prosthetic device exerts a radially outward force on an inner surface of an inner member of the expandable sheath and locally unfolds the inner member into an expanded configuration. The method also includes advancing the prosthetic device further through the lumen to a distal tip of the expandable sheath and causing a free end of a flap of the distal tip to slide circumferentially over an outer surface of a first circumferential portion of the expandable sheath to locally enlarge the lumen in response to radial pressure exerted by passage of the prosthetic device. The inner member can, in another aspect, be collapsed at the distal tip after the prosthetic device passes out of the lumen.

In other embodiments, the method can include advancing the prosthetic device through an elastomeric end extending around a distal end of the lumen to expand the elastomeric end and at least partially collapsing the elastomeric end after passage of the prosthetic device therethrough.

In other embodiments, the method can include at least partially collapsing the inner member by sliding the free end of the flap of the distal tip circumferentially over the outer surface of the first circumferential portion to locally reduce the diameter of the lumen.

Another embodiment includes an expandable sheath with a proximal seal. For example, the expandable sheath can include an elongated inner member, an elastomeric outer member and the proximal seal. The elongated inner member includes at least one foldable axial portion The outer elastomeric member extends at least partially over the inner member and is configured to exert a compressive force onto the inner member to bias the at least one foldable axial portion into a folded configuration. The proximal seal includes a middle member extending from an outer surface of the inner member to an inner surface of the outer elastomeric member. Advantageously, the seal is configured to guard against proximal migration of fluid from a distal free end of the expandable sheath to a proximal end of the expandable sheath.

In other embodiments, the inner member and outer elastomeric member can have an unconnected length distal to the proximal seal. For example, the unconnected length can extend distally from the proximal seal to the free distal end of the expandable sheath. And, the seal is thus blocking leaks by blocking a path starting at the distal free end and extending proximally along the unconnected length.

In yet other embodiments, the expandable sheath can include an outer jacket extending over the outer elastomeric member at the proximal seal's location. And, the outer elastomeric member can be fused to the inner member at the seal. The outer elastomeric member can also be foldable at the proximal seal, along with the inner member. Distal to the seal, the inner member can still be foldable independent of the outer elastomeric member. The elongated inner member—in either or both instances—can still be configured to at least partially unfold to an open configuration for passage of an implant.

In other embodiments, the elongated inner member defines a central lumen, a first circumferential portion including first and second longitudinal edges, and a second circumferential portion extending between the first and second longitudinal edges. And, the elongated inner member can be configured to crease at the first and second longitudinal edges into the folded configuration wherein the second circumferential portion is positioned at least partially between the overlapping longitudinal edges.

In other embodiments, the elongated inner member can include a distal tip, the distal tip including a flap extending from the first longitudinal edge and at least to the second longitudinal edge in an open configuration of the elongated inner member.

In other embodiments, the expandable sheath can include a proximally positioned strain relief portion. And, the proximal seal has a proximal end adjacent a distal end of the strain relief portion. The strain relief portion can have a length, for example, that is at least 9.5 cm long.

In other embodiments, a method or process of making an expandable sheath with a proximal valve is disclosed. The method includes forming a folded configuration in an elongated inner member. For example, forming a crease along a first longitudinal edge and a second longitudinal edge of the elongated inner member so that a first circumferential portion is positioned at least partially between the longitudinal edges in the folded configuration. Then, covering the elongated member with an elastomeric outer member. Also, the method can include forming a proximal seal proximal a distal free end of the expandable sheath by extending a middle member from an outer surface of the inner member to an inner surface of the elastomeric outer member.

The method can further include blocking a path, extending from a distal free end and between the inner and outer members, with the proximal seal so as to block leaks. And, fusing the elastomeric outer member to the inner member at the seal.

Fusing for example can include extending an outer jacket over the outer elastomeric member at the proximal seal. And, the method can include stretching the inner and elastomeric outer members over a mandrel into an open configuration before fusing.

Other embodiments include a method of delivering a prosthetic device. The method includes positioning an expandable sheath within the vascular system of a patient up to a proximal seal on the expandable sheath. And, further, introducing a prosthetic device into a lumen of the expandable sheath. The method can also include blocking a leak path starting at distal free end of the expandable sheath with the proximal seal. The method also includes advancing the prosthetic device through the lumen of the expandable sheath such that the prosthetic device exerts a radially outward force on an inner surface of an inner member of the expandable sheath and locally unfolds the inner member into an expanded configuration. Then, the method of delivering includes at least partially collapsing the inner member at the distal tip after the prosthetic device has passed out of the lumen of the expandable sheath.

In other embodiments, the method includes at least partially blocking the path with the proximal seal using a middle layer extending between the inner member and an outer elastomeric member.

DESCRIPTION OF DRAWINGS

FIGS. 1A-1C show side elevation views of an expandable introducer sheath (FIG. 1C) and a delivery apparatus for deployment through the sheath (FIGS. 1A-1B);

DETAILED DESCRIPTION

Figure 2:
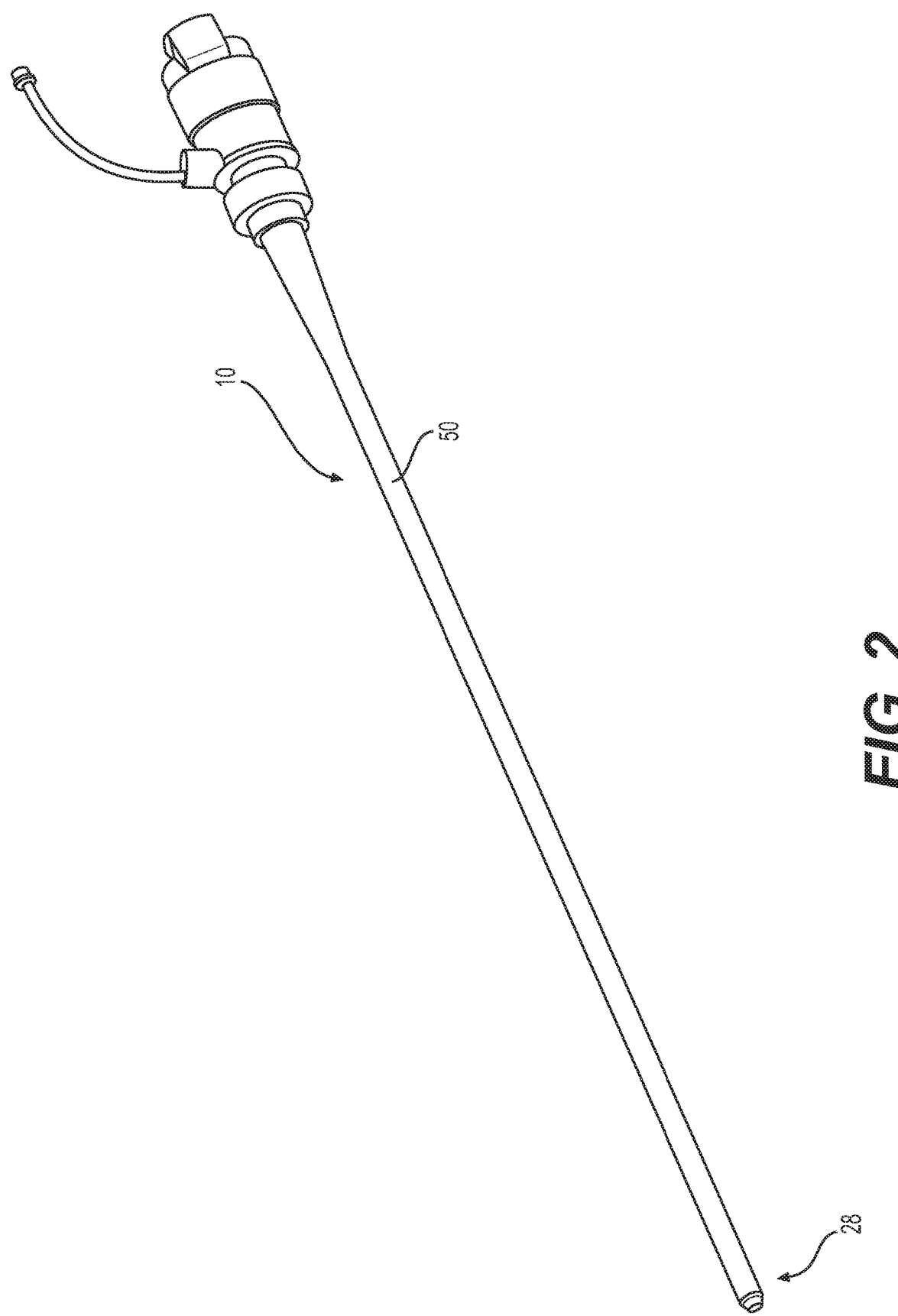
FIG. 2 shows a perspective view of an expandable introducer sheath.

The following description of certain examples of the inventive concepts should not be used to limit the scope of the claims. Other examples, features, aspects, embodiments, and advantages will become apparent to those skilled in the art from the following description. As will be realized, the device and/or methods are capable of other different and obvious aspects, all without departing from the spirit of the inventive concepts. Accordingly, the drawings and descriptions should be regarded as illustrative in nature and not restrictive.

For purposes of this description, certain aspects, advantages, and novel features of the embodiments of this disclosure are described herein. The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Features, integers, characteristics, compounds, chemical moieties, or groups described in conjunction with a particular aspect, embodiment or example of the invention are to be understood to be applicable to any other aspect, embodiment or example described herein unless incompatible therewith. All of the features disclosed in this specification (including any accompanying claims, abstract, and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract, and drawings), or to any novel one, or any novel combination, of the steps of any method or process so disclosed.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal aspect. "Such as" is not used in a restrictive sense, but for explanatory purposes.

The terms "proximal" and "distal" as used herein refer to regions of a sheath, catheter, or delivery assembly. "Proximal" means that region closest to handle of the device, while "distal" means that region farthest away from the handle of the device.

The term "tube" or "tubular" as used herein is not meant to limit shapes to circular cross-sections. Instead, tube or tubular can refer to any elongate structure with a closed-cross section and lumen extending axially therethrough. A tube may also have some selectively located slits or openings therein—although it still will provide enough of a closed structure to contain other components within its lumen(s).

The expandable introducer sheath disclosed herein is used to deliver a prosthetic device into a patient's body, through a patient's vasculature, and to a procedure site within the body. The sheath is constructed to be highly expandable and collapsible in the circumferential direction, while also minimizing the wall thickness of the sheath to minimize the profile of the delivery system. In addition, the sheath disclosed herein includes a distal tip assembly that benefits from use of a "flap" instead of a folding configuration to reduce the tip's layers to two or three while at the same time allowing for enhanced expansion diameters of 30% or more for passing implants. The flap assembly in the distal tip also allows enhanced ease of expansion for balloon and implant retrieval back through the expandable sheath. Further disclosed herein is a proximally located seal for mediating leakage of blood between the outer elastomeric layer and inner folding layer at the distal tip (blood that is between the layers due to the free edges of the flap). The seal's proximal location reduces the layers, bumps and asymmetries at the distal tip of the sheath and the seal is preferably marked for positioning at or near the site of entry into the patient's vasculature to mediate ballooning or leaks. Also, the seal assembly can include an outer jacket to enhance visibility of the seal location and guard against ballooning adjacent the seal.

FIGS. 1A-1C illustrate an expandable sheath 10 according to the present disclosure and a representative delivery apparatus 110 for delivering a prosthetic implant, such as a prosthetic heart valve, to a patient. It should be understood that the delivery apparatus 110 described herein is exemplary only, and that other similar delivery systems can of course be used with the expandable sheath 10. The delivery apparatus 110 illustrated herein generally includes a steerable guide catheter 114 and a balloon catheter 116 extending through the guide catheter 114.

The guide catheter 114 and the balloon catheter 116 illustrated in FIGS. 1A-1B are adapted to slide longitudinally relative to each other to facilitate delivery and positioning of prosthetic heart valve at an implantation site in a patient's body, as described in detail below. The guide catheter 114 includes a handle portion 120 and an elongated guide tube, or shaft, 122 extending from handle portion 120 (FIG. 1B).

FIG. 1C illustrates an expandable sheath 10 that is used to introduce the delivery apparatus 110 and the prosthetic device into the patient's body. The expandable sheath 10 has generally tubular configuration defining a central lumen to guide passage of the delivery system for the prosthetic heart valve. At a proximal end, the expandable sheath 10 includes a hemostasis valve that prevents leakage of pressurized blood. Generally, during use a distal end of the sheath 10 is passed through the skin of the patient and the sheath 10 is inserted into a vessel, such as the femoral artery. The delivery apparatus 110 (with its implant) is then inserted into the sheath 10 through the hemostasis valve, and advanced through the patient's vasculature where the implant is delivered and implanted within the patient.

Figure 3:
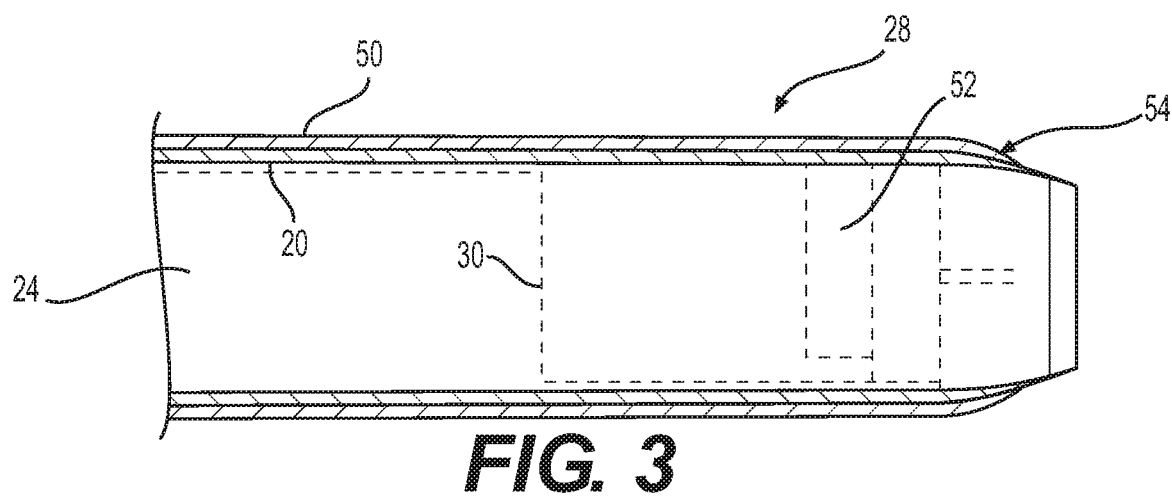
FIG. 3 shows a cross-sectional view of a distal tip of an expandable introducer sheath.
Figure 4:
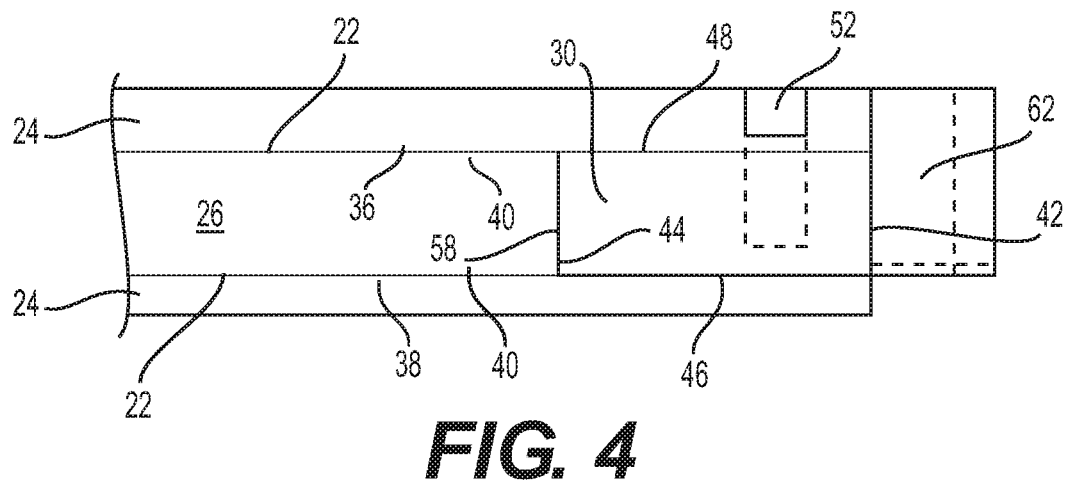
FIG. 4 shows a step in a manufacturing process of an introducer sheath including cutting a flap (sheath shown in expanded configuration)

In one embodiment, the sheath 10 includes an elongate inner member 20 and an outer elastomeric member 50 extending along a common central longitudinal axis, as shown in FIG. 2. FIG. 3 shows a cross-sectional view of a distal tip of the expandable sheath 10, and FIG. 4 shows a side view of the same distal tip in a circumferentially expanded state during a manufacturing step. As shown in FIG. 4, the elongate inner member 20 includes a first circumferential portion 24 demarcated from a second circumferential portion 26 by a pair of folds or creases 22. The creases 22 facilitate folding of the elongate member into a folded configuration. In one embodiment, a flap 30 can be cut from the second circumferential portion 26 of the inner member 20 by the following procedure. Crease 22 (corresponding to edge 38 of the second circumferential portion 26) is cut axially to create free edge 46 of flap 30. A second cut is applied generally perpendicular to free edge 46 (in a circumferential direction) to form the proximal edge 44 of flap 30. This second cut simultaneously forms distal edge 58 of the second circumferential portion 26. At this point, the flap 30 comprises a cut portion of the second circumferential portion 26 that includes a distal edge 42, a proximal edge 44, and a free edge 46.

The distal tip's 28 structure and its flap 30 allow for a reduced profile over prior art devices with built up tips. But, also, the flap 30 can promote expandability because the flap 30 is free to slide along the outside of the first circumferential portion 24. In some embodiments, the flap 30 is extended proximally and circumferentially using an extended overlap portion 60 that extends the reach of the flap 30 allowing for its greater movement relative the first circumferential portion 24. Such an extended overlap portion is shown alone in FIG. 7 and attached to the sheath 10 in FIGS. 6 and 8, and will be discussed in detail below. In another embodiment, the flap 30 can include a radiopaque marker band 52 that is applied to, embedded, or otherwise coupled to the flap 30 for the purpose of locating the distal tip of the sheath 10 inside the patient's body using radiography.

Although embodiments of the distal tip structure and proximal seal of the present invention are shown as part of a sheath with an inner folding member and an elastic outer member, other types of expandable introducer sheaths can benefit from such improvements. For example, commonly assigned U.S. patent application Ser. No. 14/880,109 (the '109 application entitled Expandable Sheath); Ser. No. 14/880,111 (the '111 application entitled Expandable Sheath with Elastomeric Cross Sectional Portions) and 62/449,454 (the '454 application entitled Expandable Sheath), which are hereby entirely incorporated herein by reference, disclose expandable introducer sheaths that can benefit from embodiments of the present invention.

In the disclosed embodiments, the sheath 10 can include an outer elastomeric member 50 encasing at least part of the length of expandable sheath 10. An example outer elastomeric member 50 is illustrated in FIGS. 1C and 2. The outer elastomeric member 50 can be formed from a variety of elastomeric materials including polyether ether ketone (PEEK), polyethylene terephthalate (PET), polyphenylene sulfide (PPS), and composite materials reinforced by carbon or glass fibers. Preferably, the outer elastomeric member 50 will be formed of biocompatible, anti-clotting materials.

When extending around the outside of the sheath 10, the outer elastomeric member 50 provides an inwardly directed radial force that serves as a fixation mechanism to prevent longitudinal slippage between the various layers of the expandable sheath 10. The compressive force provided by the outer elastomeric member 50 can also facilitate the movement of the circumferential portions of the sheath 24, 26 back toward the central longitudinal axis of the sheath 10 after their expansion by a passing prosthetic device. The sheath 10 is therefore constructed to allow for local expansion of the sheath 10 while the implant is present and then the return of the sheath 10 to its smaller, non-expanded diameter after the implant has passed through. Finally, the outer elastomeric member 50 creates a smooth surface that can minimize damage to the vascular system as the sheath 10 is being positioned and during insertion of the delivery system and implant through the sheath 10. It is contemplated that a similar inner elastomeric member (not shown) can be included extending through the central lumen of the sheath 10 to protect a passing prosthetic device from damage by the sheath 10 and to reduce friction between the sheath 10 and the device during its passage.

Embodiments of the present invention are not limited to the particular elastomeric member illustrated herein. For example, the '109, '111 and '454 applications incorporated herein by reference disclose other structure, materials and configurations for the outer elastomeric member 50. Also, although the illustrated embodiment of the outer elastomeric member 50 has a circular cross-sectional shape, other shapes are possible, such as ovals, squares and mixed or irregular shapes defining some full or partial lumen which the implant delivery device can be extended. Further, the terms "circumferential" or "circumference" or "tube" or "tubular" as used herein are not limited to circular cross-sections and instead extend to full or partial perimeters of shapes defining full or partial lumens for other layers or passage of the implants.

Figure 15:
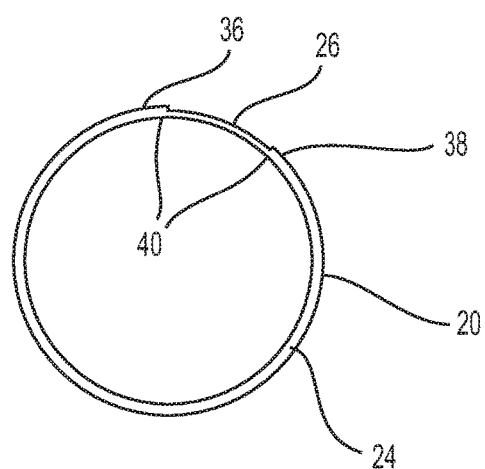
FIG. 15 is a cross-sectional view of an extruded inner member with a foldable thin wall portion.
Figure 16:
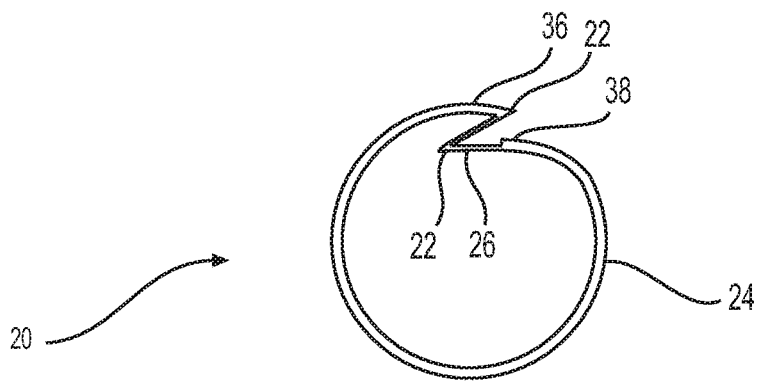
FIG. 16 is a cross-sectional view of the inner member of FIG. 15 in a folded configuration.

FIG. 15 shows a cross-section of inner member 20 in an expanded configuration illustrating the circular cross-section of the inner member 20 including the first and second circumferential portions 24, 26. FIG. 16 provides a cross section of the inner member 20 in the folded configuration, illustrating the circumferential portions 24, 26 separated from each other by a pair of fold lines or creases 22. The creases 22 extend longitudinally along most of the length of the inner member 20 (as shown in FIG. 4 and discussed above). For example, the first circumferential portion 24 includes a first longitudinal edge 36 and a second longitudinal edge 38 formed by or extending along the creases or fold lines 22. The second circumferential portion 26 has its own longitudinal edges 40 formed by the same fold lines 22 because, at least in the illustrated embodiment, it completes the perimeter of the inner member 20.

The fold lines 22 need not be straight or continuous along the length of the inner member 20. The fold lines 22 can terminate for example at or near an expanded strain relief portion for connection to the hub at the proximal end of the sheath 10. Also, the distal tip structure can include removal or modification of such fold lines. The fold lines 22 are formed in the illustrated embodiment by a reduction in wall thickness between the first and second circumferential portions 24, 26. The fold lines 22 could also be formed by scoring, conditioning, composition changes and the like to facilitate compression of the inner member 20 into a compressed, folded configuration, as shown in FIG. 16, before and after passage of an enlarging implant.

In one embodiment, the first circumferential portion 24 occupies a much greater proportion of the circular arc or perimeter of inner member 20. For example, as shown in FIG. 15, the first circumferential portion is more than three-quarters (270 degrees) of the circular cross-section of the inner member 20. The second circumferential portion 26, conversely, occupies about one-quarter or less of the remaining circumference of the inner member 20. The proportions of the first and second circumferential portions 24, 26 can be varied to fit a desired amount of reduction in the profile of the inner member 20 and remaining sheath 10. Generally, however, the illustrated proportions work well for balancing enough of the thicker first circumferential portion 24 for push strength of the sheath 10 and the amount of profile reduction afforded by the thinner second circumferential portion 26 to deliver stent-mounted heart valves and other prosthetic implants.

Figure 17:
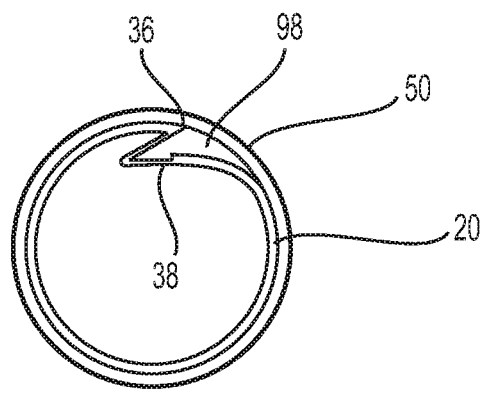
FIG. 17 is a cross-sectional view of the expandable introducer sheath with foldable inner and elastomeric outer members.

As shown in FIGS. 16 and 17, the inner member 20 has a folded configuration wherein the first longitudinal edge 36 of the first circumferential portion 24 overlaps the second longitudinal edge 38. In particular, the creases 22 facilitate—due, for example, to the urging of the elastomeric properties of the outer elastomeric member 50—folding the elongate inner member 20 into an overlapping configuration. In the overlapping configuration the longitudinal edges 36, 38 (along the creases 22) of the first circumferential portion 24 come together and pass each other into the overlapping arrangement. This arrangement also traps or enfolds portions or all of the second circumferential portion 26 between the overlapping edges of the first circumferential portion 24 so as to reduce the profile of the expandable introducer sheath 10.

The inner member 20 is preferably constructed of a tube of relatively (compared to the outer elastomeric member 50) stiff material such as a stiff polymer like high density polyethylene (HDPE) or an equivalent polymer. Integral construction, such as integral extrusion, of the wall portions advantageously avoids the leakage of prior-art sheaths that use a split in the sheath to promote expandability. Also, although the embodiment of the outer elastomeric member 50 shown in the figures has a circular cross-sectional shape, other shapes are possible, such as ovals, squares and mixed or irregular shapes as long as some form of lumen is formed through which the implant delivery device can be passed. The '109, '111 and '454 applications incorporated herein by reference disclose other structure, materials and configurations for the elongate inner member 20 that can be used with the expandable sheath disclosed herein.

Figure 5:
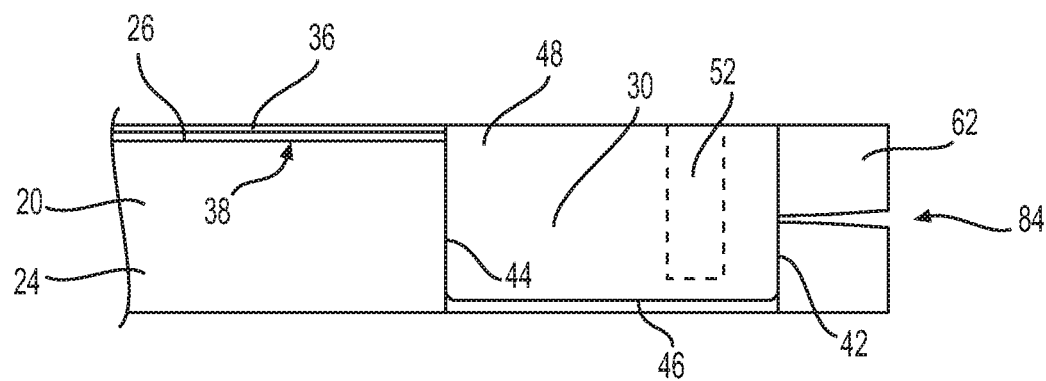
FIG. 5 shows another step of a manufacturing process of the introducer sheath including folding the sheath into a folded configuration and cutting a gap into its tip.

As shown in FIGS. 3-6, 9, and 11, the distal tip 28 of the expandable sheath in one embodiment includes the flap 30 extending a short length along the distal end of the expandable sheath 10 and ending at elastomeric free end 54. FIG. 4 shows inner member 20 in an expanded state during a manufacturing step. The illustrated flap 30 starts generally at its connected edge 48, which is located adjacent to first longitudinal edge 36 of the first circumferential portion 24. Flap 30 extends circumferentially in the direction of the second longitudinal edge 38, as shown for example in FIG. 4. As shown in FIG. 5, when sheath is folded the flap 30 extends over the second longitudinal edge 38 and back onto an outer surface of the first circumferential portion 24. Generally, the amount of overlap beyond the longitudinal edge 38 is determined by the maximum profile of the implant and delivery system.

Figure 10:
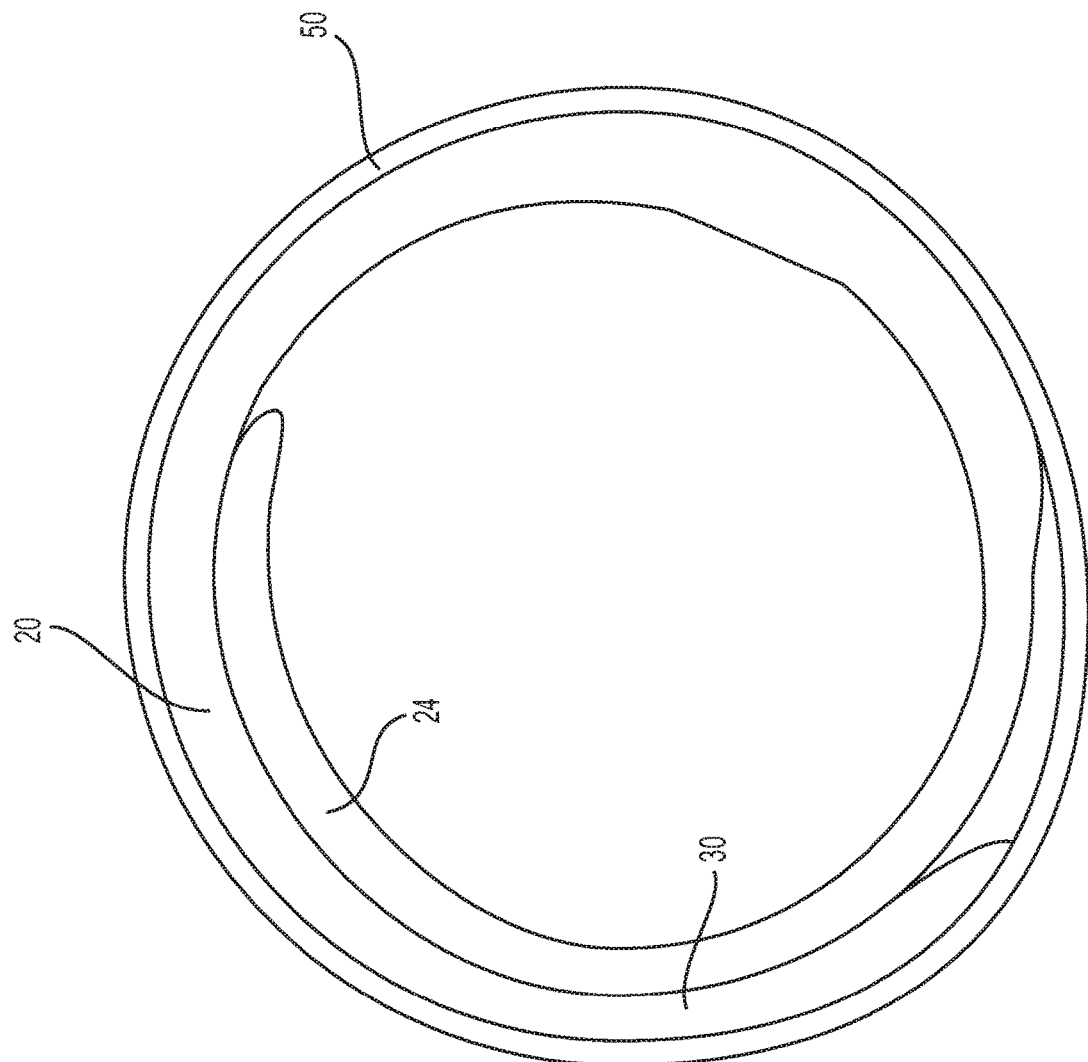
FIG. 10 is an end view of overlapping inner member and flap portions of the expandable introducer sheath without an elastomeric free end attached.
Figure 11:
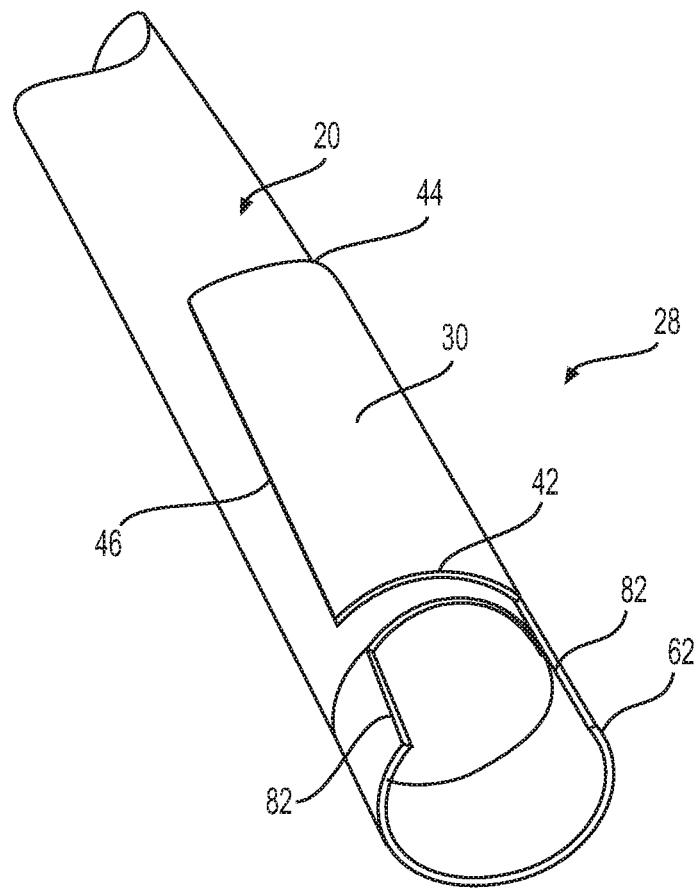
FIG. 11 is a perspective view of a sheath distal tip without an outer member and prior to bonding of the elastomeric free end.

The flap 30 includes a distal edge 42, proximal edge 44 and a free edge 46 extending between the distal and proximal edges 42, 44. A top or connected edge 48 is formed where the flap transitions, or is attached, to the first circumferential portion 24. These four edges are generally straight and connected at right angles to form a generally rectangular shape for the flap 30 (with some rounding for the corners in some embodiments). Generally, the flap 30 promotes expandability of the distal tip 28 because the flap 30 is free to slide along the outside surface of the first circumferential portion 24. As shown in FIGS. 10-11, the distal edge 42, proximal edge 44 and free edge 46 are free to slide or move with expansion and compression (folding) of the inner member 20.

The construction of the distal tip 28 advantageously avoids the need for the buildup of multiple layers used in conventional tip structures. For example, only three layers are included at the flap region of the distal tip 28, including the elastomeric outer elastomeric member 50, the flap 30, and an underlying one of the first or second circumferential portions 24, 26 of the inner member 20. In one embodiment, the flap 30 has an axial length along the free edge 46 of about 23±5 mm and a circumferential length at the distal and proximal edges 42, 44 of about 12±2 mm.

Flaps 30 of the present invention could have varied shapes and dimensions, such as square, semi-circular or other irregular shapes as long as some portion of the flap 30 extends sufficiently far axially and/or in the circumferential direction to achieve some level of overlap with the first circumferential portion 24 in at least the compressed condition. Flaps 30 can take many forms, such as a cut portion of an otherwise closed perimeter shape that is capable of temporary expansion to allow passage of implants. Or, as shown above, flaps 30 can comprise combinations of materials assembled to give different degrees of extension or overlap so as to provide the distal tip 28 with improved expandability but guard against catching when reassuming a nonexpanded or compressed configuration. The flaps 30 need not be associated only with folding sheaths, although is particularly advantageous when combined with the folding sheath disclosed herein and a valve assembly as disclosed herein to guard against fluid leaks.

Figure 9:
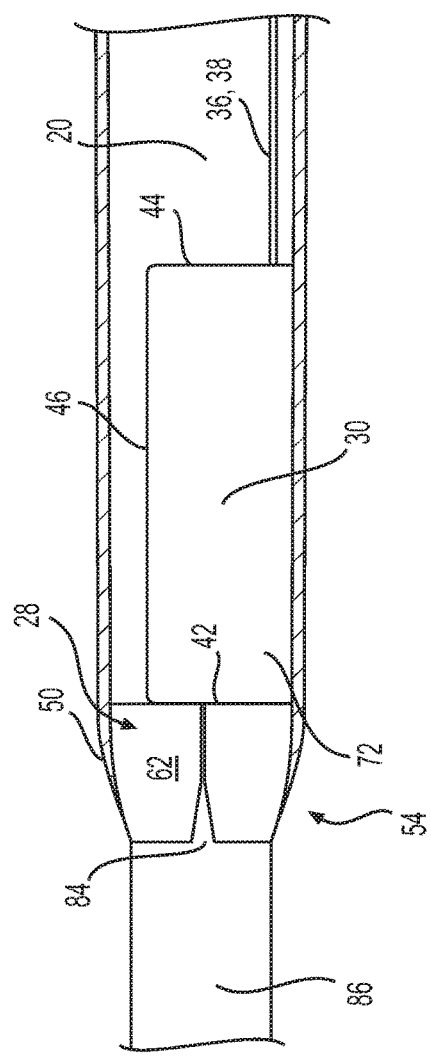
FIG. 9 shows another step of a manufacturing process including sealing the tip and an outer member of the expandable introducer sheath together.

The elastomeric free end 54 of the distal end 28 of the expandable sheath 10 preferably has an annular or tubular shape that is attached to, and extends distally from, a distal end of the first circumferential portion 24, as shown in FIG. 9, and tapers in a distal direction. Unlike the flap 30, which is free to slide, the free end 54 has sufficient elastomeric properties that it stretches to create a lumen sufficiently large for passage of the implant. Because of its annular shape, the free end 54 restrains somewhat the free expansion of the flap 30 relative to the remainder of the inner member 20. Thus, the annular shape of the free end 54 can guard against the flap 30 becoming so far displaced that its return cannot be accomplished by the outer elastomeric member 50 alone. The elastomeric free end 54 can be constructed of any elastomeric material with sufficient elasticity and fatigue resistance to manage expansion to the unfolded diameter of the sheath 10 and return. One example of such material is NEUSoft™ thermoplastic polyurethane. As shown in FIG. 9, the elastomeric free end 54 can also include a portion of the outer elastomeric member 50 bonded to an annularly configured bi-layer of NEUSoft™ and shaped into a taper at its distal end.

As shown in FIGS. 3-9, the expandable introducer sheath 10 can be constructed using a process of sectioning the inner member 20, forming a structure for the flap 30 as described above, and then bonding various layers together to form the distal tip 28. A radiopaque marker band 52 can be applied, adhered or tacked onto the inner member 20 near its distal end. Furthermore, as shown in FIGS. 9 and 11, a bilayer strip 62 formed from layers 64, 66 can be tacked to the distal edge of the inner member 20 to form part of the elastomeric free end 54. The bilayer strip 62 has a circumferential length that is the same as the circumferential length of the first circumferential portion 24. Thus, the bilayer strip 62 does not form a complete tubular layer in the expanded configuration (as demonstrated in FIG. 11). A pair of longitudinally extending free edges 82 of the bilayer strip 62 are brought together in the folded configuration and are bonded to each other with the distal end of the outer elastomeric member 50 to form the approximately annular elastomeric free end 54 (as shown in FIG. 9). The free edges 82 are then trimmed to create a gap 84 that flares slightly extending in the distal direction.

Figure 8:
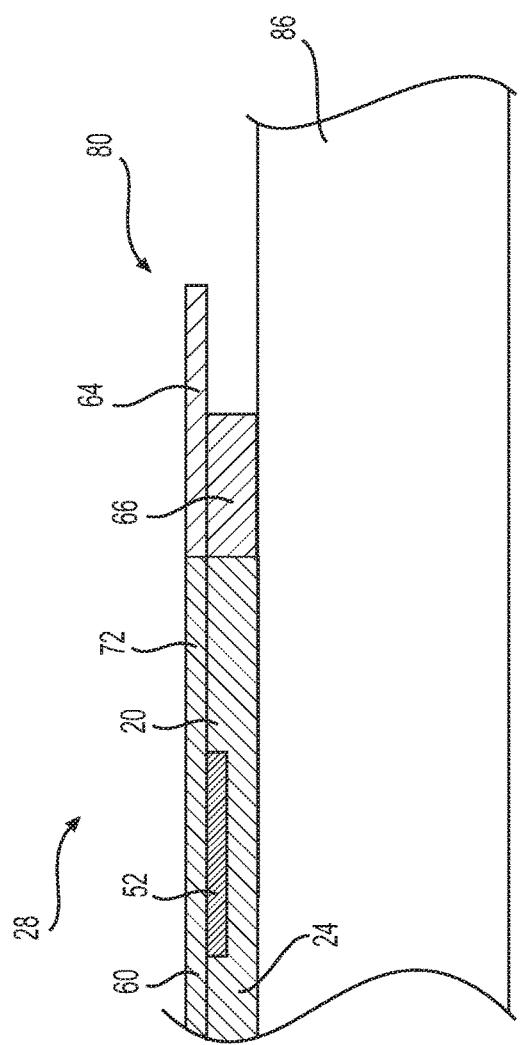
FIG. 8 shows another step of a manufacturing process including attachment of a bilayer strip to a foldable inner member.

FIG. 8 shows in cross-section that the bilayer strip 62 has an outer layer 64 that is positioned outside and extends distally past an inner layer 66. Both layers 64, 66 are positioned flush with each other at the proximal edge of the bilayer strip 62. The proximal edge of the bilayer strip 62 is heat tacked onto the distal end of the inner member 20 and the flap 30. The outer layer 64 can be thinner but longer in the axial direction than the inner layer 66. The outer layer 64, for example, can be 0.007 inch thick and 6 mm long. The inner layer 66, for example, can be 0.012 inch thick and 3 mm long. Stacked together, the total thickness of the bilayer strip 62 is slightly larger (by 0.002 inch) than the distal end of the (0.012 inch thick) first circumferential portion 24 and the 0.005 inch thick overlapping flap 30. The inner surface of the inner layer 66 and the first circumferential portion 24 are preferably flush with each other for a smooth inner lumen.

Figure 7:
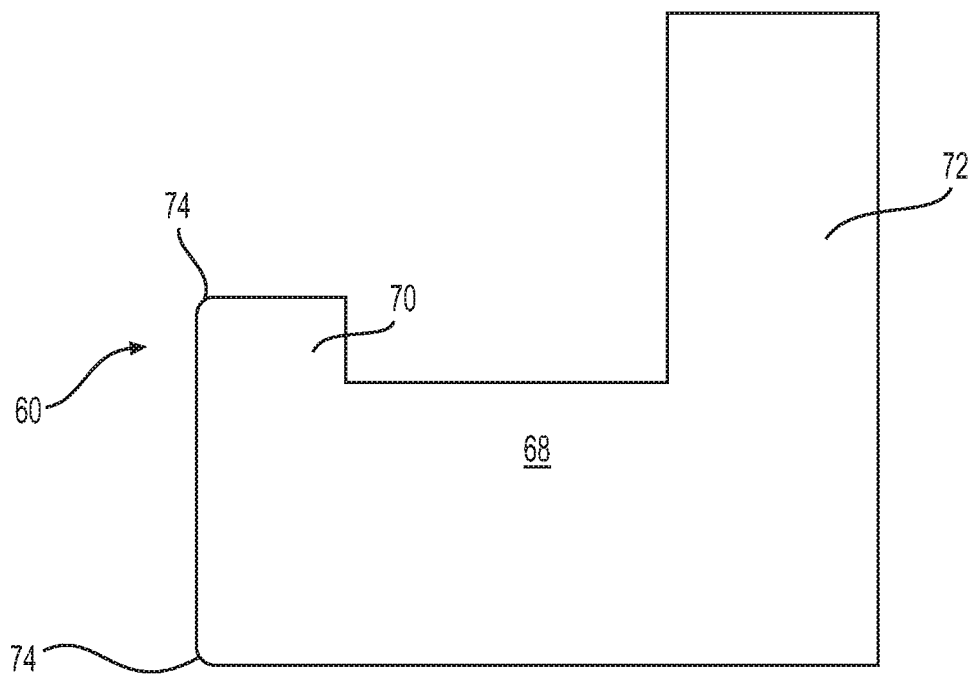
FIG. 7 shows an extended overlap for attachment to a cut flap, such as the cut flap shown in FIG. 4.

As an additional improvement, an extended overlap portion 60, such as the one shown in FIG. 7, can be attached to the cut flap 30. The extended overlap 60 has a rectangular body 68, a small tab 70 and a large tab 72 formed of a material the same or similar to the inner member 20, such as high-density polyethylene (HDPE). In one embodiment, the rectangular body 68 is approximately 11 mm by 23 mm and includes a proximal rounded corner 74. The small tab 70 extends circumferentially from the rectangular body and includes a proximal rounded corner 74. The small tab 70 has a rectangular shape and extends 3 mm in the circumferential direction from the circumferential edge of the rectangular body 68 and 5 mm in the longitudinal direction. The large tab 72 also extends circumferentially from the rectangular body 68. The large tab 72 has a rectangular shape and extends 12 mm in the circumferential direction and has an axial length of 7 mm. As a whole, then, the extended overlap 60 has a U-like shape with a long arm (the large tab 72) and a short arm (the small tab 70) that is configured to engage and extend the rectangular outside edges of the flap 30 cut from the second circumferential portion 26.

Figure 6:
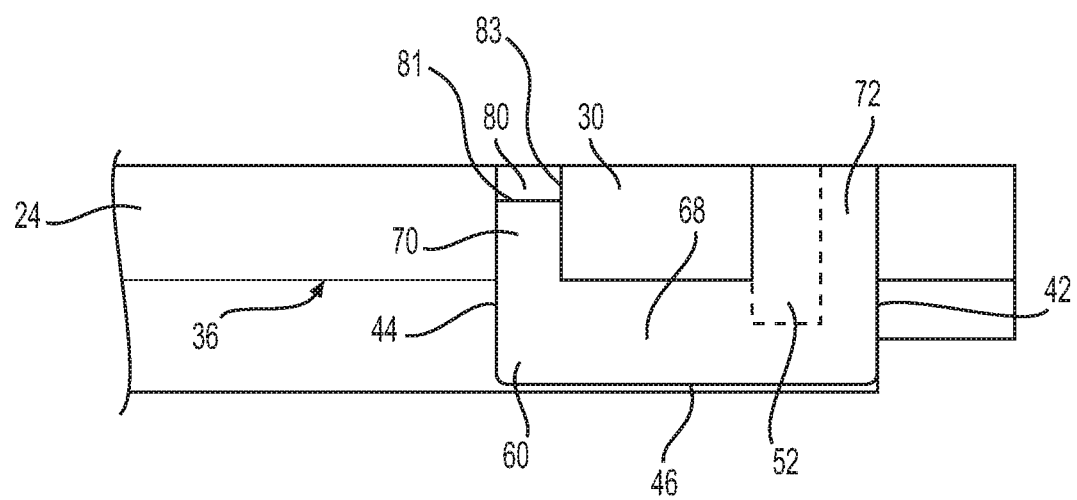
FIG. 6 shows another step of a manufacturing process of an introducer sheath including attaching an extension of the flap (sheath shown in folded configuration)

As shown in FIG. 6, the extended overlap 60 is attached (for example, by heat tacking) to the flap 30 cut from the second circumferential portion 26 to form a composite flap 30. The large tab 72 and rectangular body 68 are layered over the distal portion of the cut flap 30, covering the radiopaque marker band 52, to form the distal edge 42 of the flap 30. The small tab 70 and rectangular body 68 extend, by abutting edges, not overlapping, the proximal edge of the cut flap to form the proximal edge 44 of the flap 30. The longitudinally extending edge of the body 68 forms the free edge 46 of the flap 30.

Advantageously, the extended overlap 60 provides a larger expanse in the circumferential direction for the flap 30 to extend over the second longitudinal edge 36 (formed by crease 22) of the first circumferential portion 24 and thus cover the gap formed by cutting the flap from the second circumferential portion 26. This extends the reach of the flap 30 allowing for its greater movement relative the first circumferential portion 24 during expansion of the inner member 20, as shown in FIG. 6. Also, the flap 30 is extended in the proximal, axial direction over the distal cut edge 58 of the second circumferential portion 26.

An additional bilayer tab 80 can be tacked to the proximal edge of the cut flap 30 and circumferentially adjacent to the free end of the small tab 70. In FIG. 6, for example, the bilayer tab 80 has an axially extending edge 81 bonded to and extending circumferentially away from the top or free edge of small tab 70. The bilayer tab 80 also has a distal edge 83 bonded to the proximal edge of the cut tab 30. The bilayer tab 80 is also at least partially bonded to the outer surface of the underlying first circumferential portion 24. The bilayer tab 80 has an elastomeric composition that, because it is bonded to and connects the more stiff first circumferential portion 24 and flap 30 and flap extension 60, facilitate a smooth transition between the cut flap and the inner member 20 at the adjacent first and second circumferential portions 24, 26. The bilayer tab 80 can have a rectangular shape, such as a 2 mm by 5 mm rectangle, and a 0.007 inch and 0.012 inch layer thickness. Other shapes, sizes and thicknesses could be applied to manage the transition between the flap and adjacent inner member, although matching the thickness and using an elastomeric material has advantages of improved smoothness and elasticity.

Referring again to FIGS. 8 and 9, the cross-section shows where the large tab 72 of the extended overlap 60 (with 0.005 inch thickness) is attached onto the top surface of the underlying first circumferential portion 24 (with the 0.012 inch thickness) supporting the marker band 52. And, as described above, the proximal edge of the bilayer strip 62 is tacked to the distal edge of the built-up composite flap 30. Advantageously, the structure described above facilitates a smooth transition between the flap 30 with the extended overlap 60 and the inner member 20.

As shown in FIG. 9, the outer elastomeric member 50 is then loaded over the inner member 20 and distal tip 28 structure which are positioned on a mandrel 86. (Formation of proximal portions of the sheath 10, including the wider diameter proximal strain relief end, are shown in the '109, '111 and '454 applications incorporated herein by reference.) The outer elastomeric member 50 does not extend to the distal edge of the bilayer strip 62 to facilitate a taper in the wall thickness of the sheath 10.

On the mandrel 86, the outer elastomeric member 50 is bonded to the bilayer strip 62, and the bilayer strip 62 is completely fused to the distal edge of the inner member 20, to form the annular structure of the elastomeric free end 54. The mandrel 86 is preferably tapered to facilitate closing of the overlying gap 84 between the free edges 82 of the bilayer strip 62 and formation of the smoothly tapering frusto-conical shape of the distal tip of the sheath (shown in FIG. 2) during bonding.

Some portion of the thinner outer layer 64 of the bilayer strip 62, such as about an additional 0.5 mm to 1 mm, can extend axially beyond the distal end of the outer elastomeric member 50. This additional portion of the outer layer 64 is shaped by heat and the underlying mandrel 86 for an even more progressive tapering of the free end 54 wall thickness. Additionally, after bonding the bilayer strip 62, the process can include cutting through the bilayer and outer elastomeric member 50 at the elastomeric free end 54. Cutting through the free end wall creates a gap similar to the gap 84. Then the free end 54 can be rebounded using the mandrel 86. Advantageously, the cutting and re-bonding process selectively weakens the elastomeric free end 54 to open more easily during passage of an implant. This facilitates easier deployment and/or retrieval through the tip.

Advantageously, the tip and folding structure allows for a large difference between the expanded and nonexpanded diameters of the sheath 10. For example, the resulting final outside diameter of the sheath 10 can be as small as 19±1 French while the unfolded inside diameter is 14 French depending on the selected material wall thickness. Other advantages provided by the structure of the distal tip 28 include a more regular shape, reduced tip profile and a smoother tip transition. Also, the fewer layers and elastomeric free end 54 help to reduce push force through the tip. Formation and extension of the flap 30 opens up the inner member 20 and facilitates opening of the tip to greater diameters than the proximal end of the inner member, for example 30% or greater expansion over the folded diameter. This lowers forces and improves reliability of balloon, valve and other implant retrieval.

Figure 12:
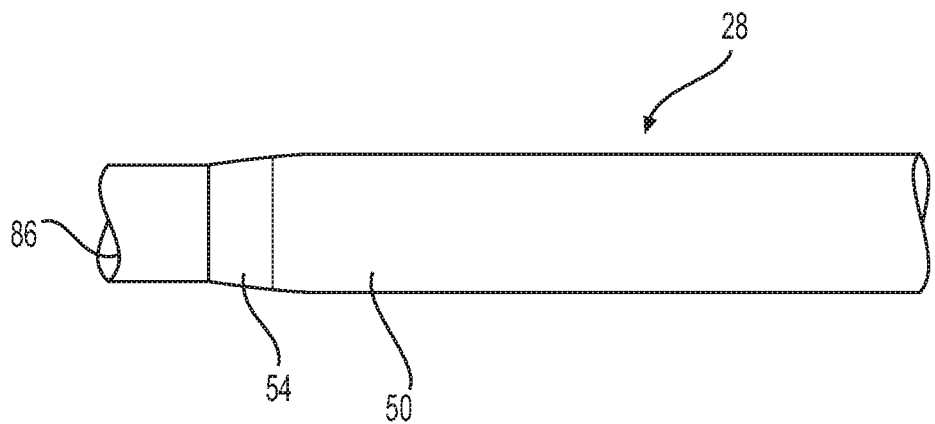
FIG. 12 is a side elevation view of a profile of a distal tip of an expandable introducer sheath in a folded configuration on a mandrel.
Figure 13:
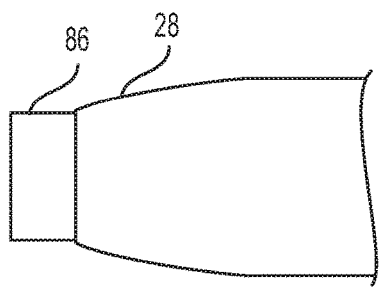
FIG. 13 is an enlarged view of a leading edge of the sheath shown in FIG. 12.

FIG. 12 shows the smooth transition of the distal tip 28—with a steadily decreasing diameter—to the final diameter of the distal-most edge of the sheath 10. FIG. 13 shows also the relatively small step down from the distal end of the sheath 10 to the mandrel 86. Thus, the distal tip 28 can provide much greater expansion capability without a substantial increase in step height, angle of taper or outer diameter at the end of the sheath 10.

Various embodiments of the distal tip 28 include various advantages, such as elimination of splits in the sheath, lifting of the folding edge and tip delamination. Also, the distal tip 28 can better receive a larger deflated balloon profile for the retrieval of the delivery system. Further, the distal tip 28 can provide an improved tip profile, recovery capability, and circularity during recovery. Tip transition smoothness is improved, as well as push forces reduced and made more consistent, by embodiments of the distal tip 28.

Figure 14:
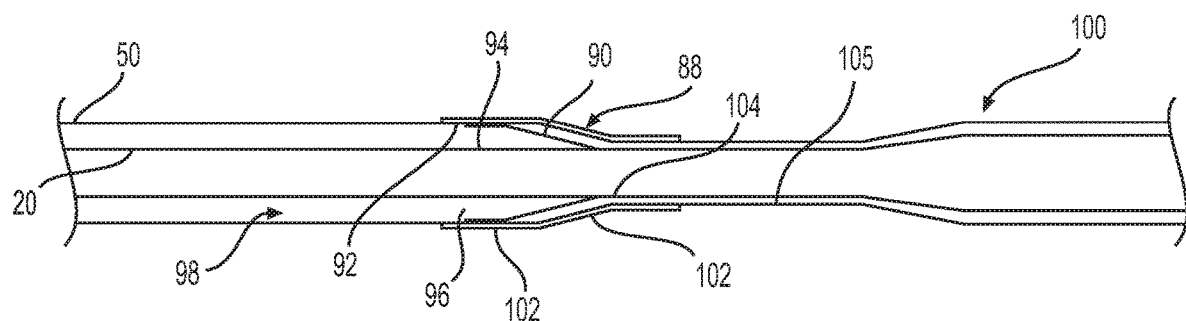
FIG. 14 is a schematic of an expandable introducer sheath with a proximally positioned seal.
Figure 22A:
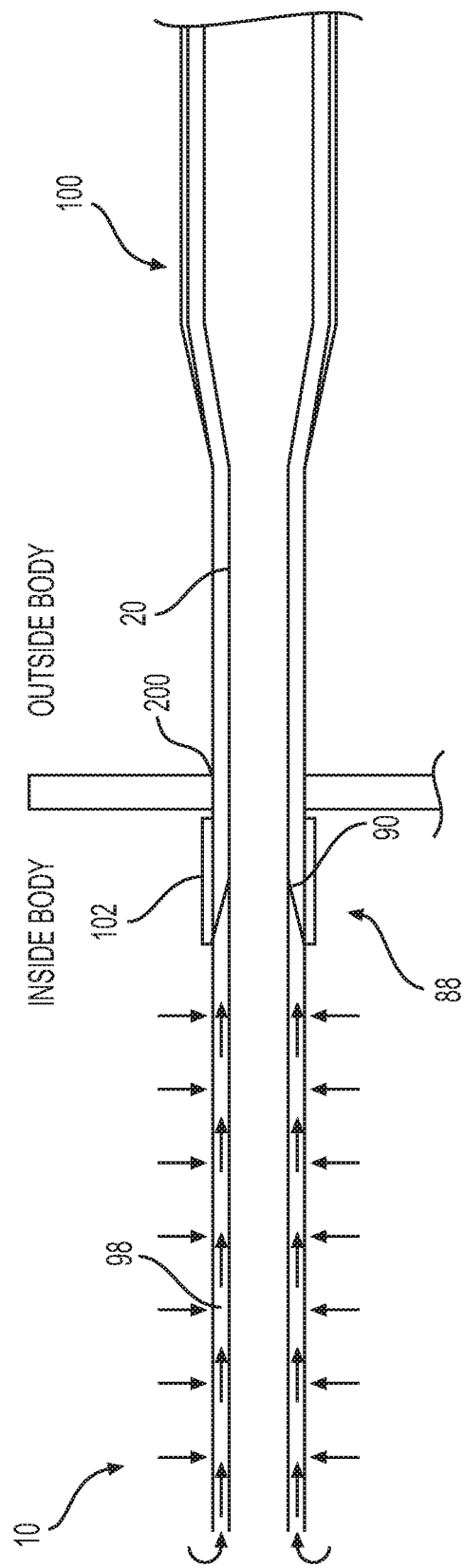
FIGS. 22A and 22B are schematics of an expandable introducer sheath with a proximal valve being withdrawn from a patient.
Figure 22B:
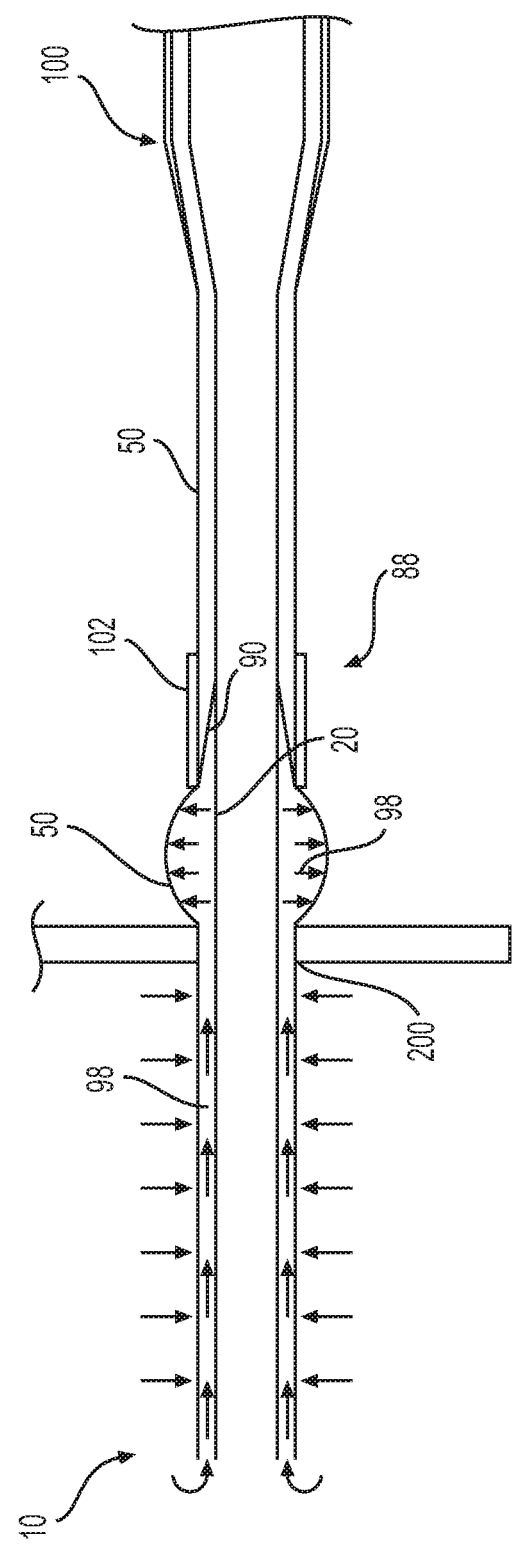

In another embodiment, the expandable introducer sheath 10 can include a proximal hemostasis seal assembly 88, as shown in FIGS. 14, 22A and 22B. The proximal positioning of the seal assembly 88—away from the distal tip of the expandable sheath 10—reduces the size of the distal tip, smooths the profile of the distal tip and allows the flap 30 to slide more freely than if it were sealed. The proximal seal assembly 88 is particularly advantageous when used with the flap assembly 30 because the flap assembly's structure can allow invasion of fluids from the patient between the layers of the sheath 10.

The proximal seal assembly 88, for example, can include a middle member 90 that extends from an inner surface 92 of the outer elastomeric member 50 to an outer surface 94 of the inner member 20. As shown schematically in FIG. 14, the middle member 90 has an expanded, open distal end 96 with an outer surface that is connected to the inner surface 92 of the outer elastomeric member 50, such as by tacking or bonding. The middle member 90 tapers in the proximal direction to an annular attachment to the outside surface 94 of the inner elongate member 20.

The open distal end 96 of the proximal seal assembly 88 is not connected to the inner member 20 of the sheath 10 and can receive fluid from a leak path 98 between the members 20, 50, as shown in FIG. 17. The leak path 98 extends, therefore, between the inner surface 92 of the outer elastic member 50 and the outer surface 94 of the inner member 20. The leak path 98 can include the space between the overlapping edges 36, 38 of the first circumferential portion 24 up to the proximal attachment of the middle member 90 to the inner member 20. The leak path 98 extends from the free edges of the inner member 20 and elastomeric member 50 where they are unconnected to each other and proximally to the attachment of the middle member 90 to the inner member at a closed proximal end 104, as shown in FIG. 22A.

Stated differently, the unconnected or unattached length extends distal to the middle member's 90 attachment to the inner member 20 to the free, unattached edges of the inner member 20, outer elastomeric member 50 and any other layers or members not attached to each other and thereby allowing full or partial invasion of fluid in a leak path. As shown in FIG. 22B, the leak path 98 can cause some ballooning effects to the portions of the outer elastic member 50 outside the body since it allows blood pressure to reach the outer elastomeric member 50 (without countervailing body fluid pressure forces to offset the blood pressure). Although not entirely deleterious, ballooning should be curbed or avoided to minimize the chance of leaks.

Although the illustrated leak path 98 has the above-described characteristics, it should be noted that the seal assembly 88 could be employed without any leak path or the leak path could be different than between the two members 20, 50. Leaks can also occur due to tearing or pin holes forming under arterial blood pressure to the elastomeric member 50 and be managed by the proximal seal assembly. Generally, the middle member 90 is shown as a tubular member with distal and proximal cylindrical portions connected by a tapering conical region in the middle. It should be noted, however, that the seal assembly 88 could be constructed of a range of materials, layers and members and achieve the end of mediating proximal migration of leaks. For example, a disc-shaped plug can be employed that extends between the inner surface 92 and outer surface 94 so as to block the leak path. Or, multiple layers could be used, employing several of the middle members in combination with plugs. Or, as another example, a duckbill style valve could be employed to maintain some movability in the axial direction between the members 20, 50.

The proximal positioning of the proximal seal assembly 88 is generally more proximal than the distal tip 28 including the flap 30. In the illustrated embodiment, the proximal seal assembly 88 is adjacent to or slightly distal to a strain relief portion 100 of the sheath, as shown in FIG. 14. In any case, generally, the more proximal the positioning of the proximal seal assembly 88, the easier it is to operate the expandable introducer sheath 10 because a bump, irregularity or thickening due to the seal is present only for a short insertion length (FIG. 22A) or is entirely outside the body, as shown in FIG. 22B. But, at the same time, the more distal the positioning of the proximal seal assembly 88, the better it is suited for positioning at or just inside the percutaneous opening 200 in the body, as shown in FIG. 22A. With such positioning, any ballooning (FIG. 22B) that can arise from the blood pressure in the leak path 98 exerting expansion forces on the elastic outer elastomeric member 50 can be reduced, minimized or eliminated. In embodiments used for femoral access to the aortic valve, the proximal seal assembly 88 can be located 9.5 cm or further from the housing at the proximal end of the device and about at the end of the strain relief portion 100.

Figure 20:
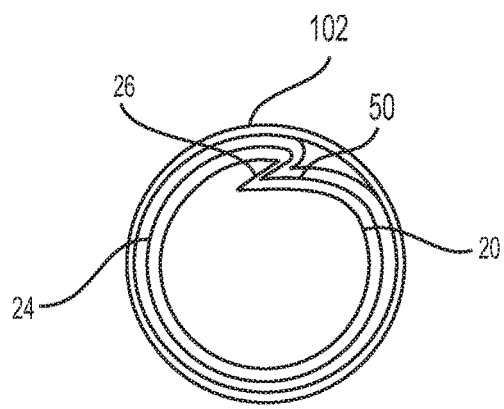
FIG. 20 is a cross-sectional view of the introducer sheath of FIG. 19 in a folded configuration.

As shown in FIG. 14, the expandable sheath 10 can also include a fused portion 105. In particular, the fused portion 105 is where the elastomeric member 50 has been fused or attached to the inner member 20. The fused portion 105 starts at and extends proximally from the closed proximal end 104 of the seal. As shown in FIG. 20, this fusion allows the outer elastomeric member 50 to fold along with the inner member 20 into the folded configuration and further blocks against leakage between the members 20, 50. The seal assembly 88 can also include an outer jacket 102 that has a tubular shape and extends along an axial portion of the sheath 10 overlapping the middle member 90 of the seal. The outer jacket 102 is preferably of an elastomeric material and is used to urge the fused portions of the inner member 20 and outer elastomeric member 50 into the collapsed configuration and to urge blood out between the members at the open distal end 96. Further, the outer jacket 102 can include a marker to indicate the depth at which the user can advance the sheath 10 to minimize or eliminate ballooning.

Figure 18:
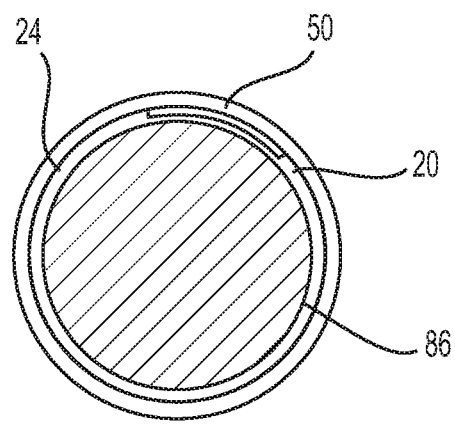
FIG. 18 is a cross-sectional view of an unfolded or expanded introducer sheath on a mandrel.

Generally, FIGS. 15-21 illustrate a proximal seal manufacturing process. In FIG. 15, an inner member 20 is extruded or otherwise provided including the first and second circumferential portions 24, 26. In FIG. 16, the inner member 20 is conditioned via repeated folding into the folded or compressed configuration. In FIG. 17, the elastomeric outer layer 50 is sleeved over the outside surface of the inner member 20 in its folded configuration. In FIG. 18, the inner member 20 is opened into the unfolded configuration through insertion of a mandrel 86 into the lumen of the inner member. The outer elastomeric member 50 is also expanded (stretched) against its elastomeric bias into the expanded, unfolded configuration.

Figure 19:
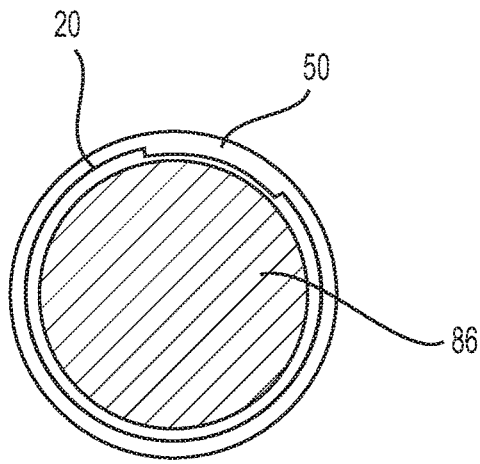
FIG. 19 shows is a cross-sectional view of an unfolded or expanded introducer sheath wherein the inner and outer members are bonded together.
Figure 21:
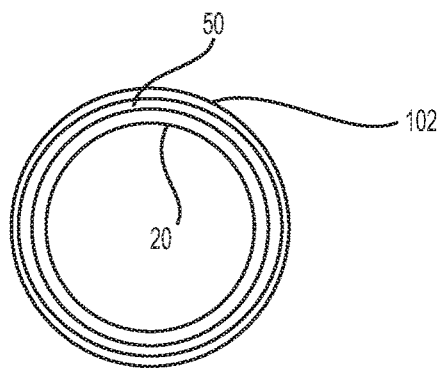
FIG. 21 is a cross-sectional view of the introducer sheath of FIG. 20 including an outer jacket.

In FIG. 19, the outer elastomeric member 50 is fused to the outside surface of the inner member 20 (at least at the proximal seal assembly 88 location). FIG. 20 shows the fused assembly being folded—including the outer elastomeric member 50—into the folded configuration and includes the addition of an elastomeric outer jacket 102. FIG. 21 shows the fused assembly in an expanded configuration. Notably, the closed proximal end 104 of the seal 88 could also be formed by fusing the middle member 90 to the inner member 20 to form the closed proximal end 104 and fusing the middle member 90 to the outer elastomeric member 50 to form the open distal end 96. In any case, the leak path 98 is sealed at least partially against proximal migration of fluids.

The outer jacket 102 can be configured to give a visual indicator of when the valve assembly 88 has been advanced close or into the patient to guard against leakage and/or to provide additional restraint against ballooning of the outer elastomeric member 50 around the leak path. For example, the outer jacket 102 can be constructed of a NEUSoft band that is then pen or cold laser marked to illustrate the depth at which the sheath 10 is advanced within the patient's body. The axial length of the outer jacket for example can be 1⅛ inch with the seal length being ⅝ inch. A distal portion of the outer jacket 102 can extend, for example, ⅛ inch further than the distal end of the seal assembly 88 while an additional ⅜ inch is present on the proximal end of the seal assembly 88 for some safety margin.

As described above, the expandable sheath 10 can be used to deliver, remove, repair, and/or replace a prosthetic device. In one example, the sheath 10 described above can be used to deliver a prosthetic heart valve to a patient. For example, after the sheath 10 is inserted into the body and into the patent's vasculature, a heart valve (in a crimped or compressed state) mounted on the distal end portion of an elongated delivery catheter is inserted into the sheath. Next, the delivery catheter and heart valve can be advanced through the sheath and through the patient's vasculature to the treatment site, where the valve is implanted.

In particular, when the sheath 10 is used to deliver the implant, the flap 30 of the distal tip 28 expands to a much larger diameter than just unfolding the elongate inner member 20 for easy deployment and retrieval of balloons and implants. As the implant is passed through the distal tip 28, the free edge 46 of the flap 30 rides up the outside surface (under outer elastomeric member 50) to expand the space in the tip. The elastomeric free end 54 also expands to accommodate the implant. The distal tip 28 can expand again during retrieval of the delivery device or retrieved implant, with the flap 30 once again sliding freely at the proximal, distal and free edges 42, 44 and 46 to easily receive the deflated balloon or retrieved implant.

Further, while the expandable sheath 10 is advanced in the high pressure of the patient's arteries, the blood extends into the leak path 98 but is blocked by the seal assembly 88. As shown in FIGS. 22A and 22B, the sheath 10 is advanced until the outer jacket 102 abuts or extends into the inside of the patient's body. This reduces or eliminates ballooning of the outer elastomeric member 50 due to the pressure of the blood or other body fluids.

Beyond transcatheter heart valves, the expandable sheath 10 can be useful for other types of minimally invasive procedure, such as any procedure requiring introduction of an apparatus into a subject's vessel. For example, the expandable sheath 10 can be used to introduce other types of delivery apparatus for placing various types of intraluminal devices (e.g., stents, stented grafts, balloon catheters for angioplasty procedures, etc.) into many types of vascular and non-vascular body lumens (e.g., veins, arteries, esophagus, ducts of the biliary tree, intestine, urethra, fallopian tube, other endocrine or exocrine ducts, etc.).

Although the foregoing embodiments of the present disclosure have been described in some detail by way of illustration and example for purposes of clarity and understanding, it will be apparent to those skilled in the art that certain changes and modifications may be practiced within the spirit and scope of the present disclosure. It is intended that the scope of the present invention herein disclosed should not be limited by the particular disclosed embodiments described above, but should be determined only by a fair reading of the claims that follow.

What is claimed is:

1. A method of making an expandable sheath, the method comprising:
   forming a folded configuration in an elongated inner member by forming a crease along a first longitudinal edge and a second longitudinal edge of the elongated inner member so that a first circumferential portion is positioned at least partially between the first and second longitudinal edges in the folded configuration;
   covering the elongated inner member with an elastomeric outer member; and
   forming a proximal seal proximal a distal free end of the expandable sheath by extending a middle member from an outer surface of the elongated inner member to an inner surface of the elastomeric outer member, thereby blocking a flow path extending between the elongated inner member and the elastomeric outer member with the proximal seal and forming a distal portion of the flow path between the elongated inner member and the elastomeric outer member extending from the distal free end of the expandable sheath to the proximal seal;
   wherein the distal portion of the flow path is in fluid communication with an opening between the elongated inner member and the elastomeric outer member at the distal free end of the expandable sheath.

2. The method of claim 1, further comprising fusing the elastomeric outer member to the elongated inner member at the proximal seal.

3. The method of claim 2, wherein the elastomeric outer member is fused to the elongated inner member such that the distal portion of the flow path is formed distal the proximal seal.

4. The method of claim 1, further comprising an outer jacket extending over the elastomeric outer member at the proximal seal.

5. The method of claim 4, further comprising fusing the elastomeric outer member to the elongated inner member at the proximal seal.

6. The method of claim 5, wherein the elastomeric outer member is foldable at the proximal seal along with the elongated inner member.

7. The method of claim 6, wherein the elongated inner member is foldable independent of the elastomeric outer member distal to the proximal seal such that the elongated inner member is configured to at least partially unfold to an open configuration for a passage of an implant.

8. The method of claim 1, further comprising forming a strain relief portion extending distally from a proximal end of the expandable sheath and wherein the proximal seal has a proximal end adjacent a distal end of the strain relief portion.

9. A method of making an expandable sheath, the method comprising:
   forming a folded configuration in an elongated inner member by forming a crease along a first longitudinal edge and a second longitudinal edge of the elongated inner member so that a first circumferential portion is positioned at least partially between the first and second longitudinal edges in the folded configuration;
   covering the elongated inner member with an elastomeric outer member; and
   forming a proximal seal proximal a distal free end of the expandable sheath by extending a middle member from an outer surface of the elongated inner member to an inner surface of the elastomeric outer member, thereby blocking a flow path extending between the elongated inner member and the elastomeric outer member with the proximal seal and forming a distal portion of the flow path between the elongated inner member and the elastomeric outer member extending from the distal free end of the expandable sheath to the proximal seal;

wherein the distal portion of the flow path is in fluid communication with an opening between the elongated inner member and the elastomeric outer member at the distal free end of the expandable sheath;

wherein the proximal seal is configured to block the flow path starting at the distal free end and extending proximally to the proximal seal.

10. The method of claim 9, further comprising fusing the elastomeric outer member to the elongated inner member at the proximal seal.

11. The method of claim 10, wherein the elastomeric outer member is fused to the elongated inner member such that the distal portion of the flow path is formed distal the proximal seal.

12. The method of claim 9, further comprising an outer jacket extending over the elastomeric outer member at the proximal seal.

13. The method of claim 12, further comprising fusing the elastomeric outer member to the elongated inner member at the proximal seal.

14. The method of claim 13, wherein the elastomeric outer member is foldable at the proximal seal along with the elongated inner member.

15. The method of claim 14, wherein the elongated inner member is foldable independent of the elastomeric outer member distal to the proximal seal such that the elongated inner member is configured to at least partially unfold to an open configuration for a passage of an implant.

16. The method of claim 9, further comprising forming a strain relief portion extending distally from a proximal end of the expandable sheath and wherein the proximal seal has a proximal end adjacent a distal end of the strain relief portion.

* * * * *